United States Patent [19]
Watson et al.

[11] Patent Number: 5,643,185
[45] Date of Patent: Jul. 1, 1997

[54] KNEE AND ELBOW JOINT BRACE

[76] Inventors: Randy C. Watson, 599 Lake Tahoe Blvd. Aspen Building, Suite B-1, South Lake Tahoe, Calif. 96150; Richard L. Bajocchi, 630 Alma Way, Zephyr Cove, Nev. 89448

[21] Appl. No.: 550,608

[22] Filed: Oct. 31, 1995

[51] Int. Cl.⁶ .................................................. A61F 5/00
[52] U.S. Cl. .......................... 602/26; 602/13; 602/63
[58] Field of Search ........................ 602/5, 6, 13, 19, 602/23, 26, 61–63; 128/DIG. 20; 601/151; 607/108–112

[56] References Cited

U.S. PATENT DOCUMENTS

| | | | |
|---|---|---|---|
| 4,201,203 | 5/1980 | Applegate | 602/26 |
| 4,378,009 | 3/1983 | Rowley et al. | 602/13 |
| 4,700,698 | 10/1987 | Kleyleon | 602/26 |
| 4,938,207 | 7/1990 | Vargo | 602/26 |
| 5,334,135 | 8/1994 | Grim et al. | 602/13 X |
| 5,378,224 | 1/1995 | Billotti | 602/13 |
| 5,383,843 | 1/1995 | Watson et al. | 602/13 |
| 5,451,201 | 9/1995 | Prengler | 602/13 X |
| 5,527,267 | 6/1996 | Billotti | 602/13 |

*Primary Examiner*—Linda C. Dvorak
*Attorney, Agent, or Firm*—Thomas N. Neiman

[57] ABSTRACT

The novel portable knee and elbow joint apparatus is comprised of a unit that is designed to allow the individual using the apparatus a self determined amount of support pressure by the apparatus in those joints. The apparatus has a bladder chamber that channels air in the bladder in such a manner that optimizes the support shape around the elbow and knee joints. A plastic spring check valve attached to a flexible bulb directs the air into the bladder and maintains the air therein. The apparatus is composed of flexible material that wraps around the joint and positions the open bladder around joint. A fiber mesh covers the top of the bladder. Reinforcement stays are positioned vertically at each side of the brace apparatus in order to maintain the shape of the apparatus.

3 Claims, 2 Drawing Sheets

KNEE AND ELBOW JOINT BRACE

BACKGROUND OF THE INVENTION

This invention pertains to joint support devices, and in particular, to such knee and elbow joint brace apparatus that are designed to allow the user to protect and support the knee and elbow joints with the amount of pressure that the individual can set by himself or herself.

Many types and designs of joint braces are currently on the market. There have been many of these devices that have been patented. Examples of these devices include the U.S. Pat. No. 4,700,698 to Horst Kleylein for a Knee Orthosis which issued on 20 Oct. 1987, the United States Patent issued to Otis E. Harper, U.S. Pat. No. 4,425,912 for a Knee Protector/Stabilizer issued on 17 Jan. 1984 and the United States Patent issued to Randy C. Watson and Richard L. Baiocchi on 24 Jan. 1995 for an Air Pressure Knee Brace Apparatus. These devices show different approaches in tightening and loosening the pressure around a knee joint with only the Watson and Baiocchi device using air pressure to accomplish this goal. What is needed is a lightweight device that an individual can easily fold and store and, at the same time, be readily available and be able to use on the elbow and knee joints with no inconvenience.

Clearly, it is desirable for a device of this type to be very lightweight. At the same time, the device should be easy to manufacture and be produced of inexpensive material. It is the object of this invention to set forth a knee and elbow joint brace apparatus which avoids the disadvantages, previously mentioned limitations of typical joint braces.

SUMMARY OF THE INVENTION

Particularly, it is the object of this invention to teach a knee and elbow joint brace apparatus, for use in providing a lightweight protection and support unit for individuals desiring firm protection and support, comprising flexible means; said flexible means comprising a stretchable wrapping portion to be positioned around the back of a joint area of an individual; said flexible means having at least one sizing means as desired by the individual using the apparatus; a pneumatic chamber attached to said flexible means to be positioned over the joint area forming an encircling means around the joint area; said pneumatic chamber having mesh means for attaching and positioning said pneumatic chamber to said apparatus; said pneumatic chamber having an aperture located at the center of said pneumatic chamber to be positioned over the joint to allow freedom of movement by said joint; said pneumatic chamber further having air flow direction means for assisting the ideal shape for said pneumatic chamber; said pneumatic chamber further having valving means for permitting the inflation and deflation of said pneumatic chamber as desired by the individual using said apparatus; and shape enhancing means for maintaining the shape of said knee and elbow joint brace apparatus.

BRIEF DESCRIPTION OF THE INVENTION

Further objects and features of this invention will become more apparent by reference to the following description taken in conjunction with the following figures, in which.

DESCRIPTION OF THE PREFERRED EMBODIMENTS

Figure 1:
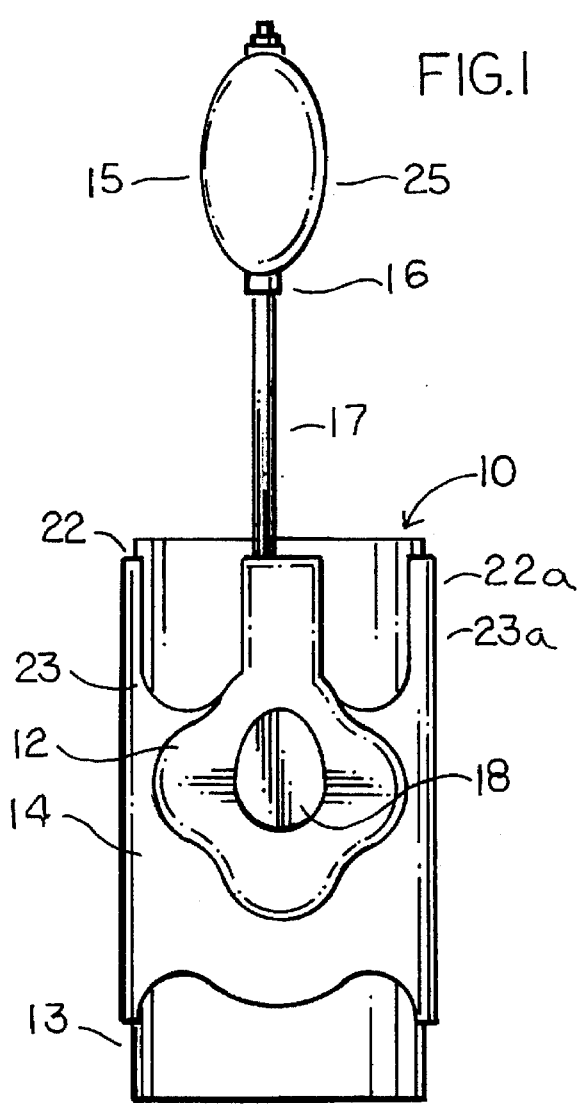
FIG. 1 is a top plan view of the novel knee and elbow joint brace apparatus.
Figure 2:
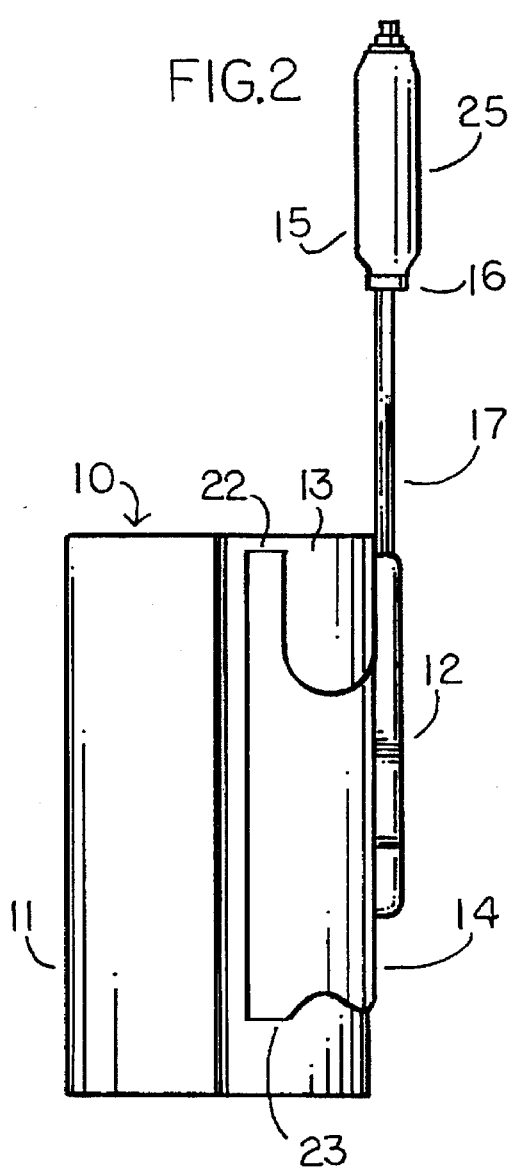
FIG. 2 is a side elevation view thereof.
Figure 3:
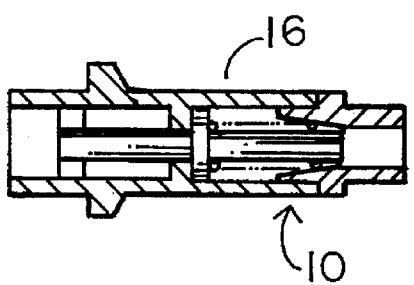
FIG. 3 is a side elevational view of the plastic spring check valve of the novel apparatus.
Figure 4:
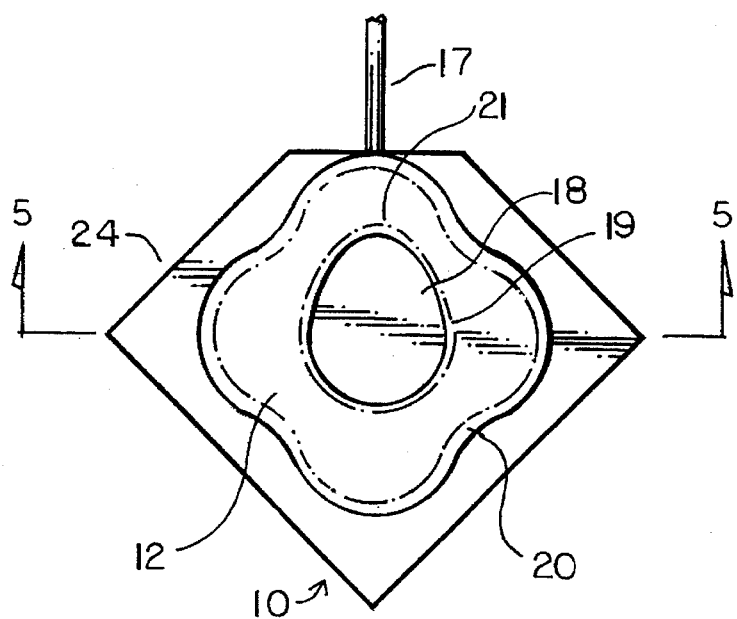
FIG. 4 is a top plan view of the pneumatic chamber of the apparatus.
Figure 6:
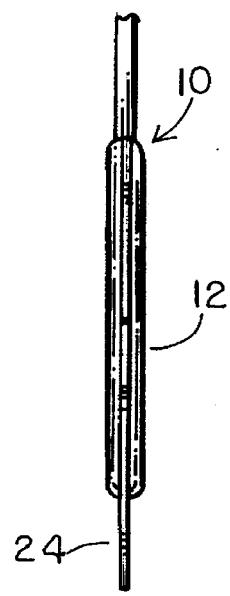
FIG. 6 is a side elevational view of the pneumatic chamber.
Figure 5:
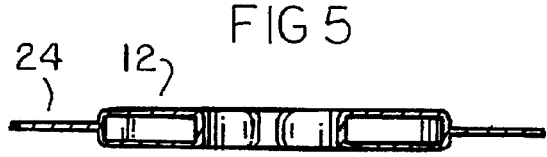
FIG. 5 is a cross sectional view of the pneumatic chamber taken along line 5—5 of FIG. 4.

As shown in the figures, the novel knee and elbow joint brace apparatus 10 comprises a flexible material wrap 11 which fits around the back of the joint. The material can be neoprene or perforated neoprene or the like. The wrap can be constructed of mesh material in order to improve the cooling characteristics of the apparatus 10. The apparatus 10 is fitted over the joint and the stretchable characteristics of the material control the hold of the apparatus along with the inflation and deflation of the chamber 12. The front section of the apparatus 10 is comprised of a combination of flexible material 13, the chamber 12 constructed of latex rubber that is covered with a soft material 14 which is sewed to attach the pneumatic chamber 12 in position on the flexible material 13. A mesh portion of material 24 covers, the outer edges of the pneumatic chamber 12 in order to hold the shape of the chamber in solid position.

The pneumatic chamber 12 has a valving unit 15 which is comprised of a connecting tube 17 which is attached to a plastic spring check valve 16 that is designed to allow air into the chamber 12 when the bulb 25 is squeezed on one end and releases air when the other end of the bulb 25 is inserted into the spring check valve 16 and is squeezed. The valving unit 15 is engineered with a built in check valve which when squeezed allows air to flow into the pneumatic chamber 12. When the other end of the bulb is attached to the inflation tube the check valve in the pneumatic chamber allows air to escape from the pneumatic chamber 12. The bulb 25 can be disconnected from the plastic spring check valve 16. The pneumatic chamber has an aperture 18 that is positioned over the joint to allow freedom of movement of the joint. The area of the pneumatic chamber 12 around the aperture has an incision made and hard rubber patches 19 are inserted in order to close the center aperture. Also the outer edges are also reinforced with a layer of hard rubber 20. The chamber itself is contoured at the top end 21 to an oblong shape to allow for better biomedical function of the patella and its quadriceps mechanism. Spiral wire stays 22 and 22a are inserted in pockets 23 and 23a on each side of the pneumatic chamber to assist the apparatus in maintaining its shape.

In operation, the individual desiring the support and protection for the kneecap or elbow, would slide the apparatus up into position around the joint. The air pressure would then be built up through the valving unit. The user would adjust the air pressure to provide user with as much support and protection and, at the same time, allow as much comfort as desired.

While we have described our invention in connection with specific embodiments thereof, it is clearly to be understood that this is done only by way of example and not as a limitation to the scope of our invention as set forth in the objects thereof and in the appended claims.

We claim:

1. A knee and elbow joint brace apparatus, for use in providing a lightweight protection and support unit for individuals desiring firm protection and support, comprising:

flexible means;

said flexible means comprising stretchable wrapping portion to be positioned around the back of the joint area of an individual;

said flexible means further comprising a brace that can expand as necessary to enable the apparatus to fit around the limbs of an individual;

said flexible means having at least one sizing means for tightening or loosening said flexible means as desired by the individual using the apparatus;

said sizing means comprising at least one open and closed loop strapping device to permit tightening and loosening said apparatus;

a pneumatic chamber attached to said flexible means to be positioned over the joint area forming an encircling means around the joint area;

said pneumatic chamber comprising an expandable unit that is attached to said front portion of said flexible means to create an encircling unit around the joint area;

said pneumatic chamber having mesh means for attaching and positioning said pneumatic chamber to said apparatus;

said mesh means of said pneumatic chamber comprising which covers at least part of the top of said pneumatic chamber and is attached to said flexible material;

said pneumatic chamber having an aperture located at the center of said pneumatic chamber to be positioned over the joint to allow freedom of movement by said joint;

said aperture in said center of said pneumatic chamber comprising a circular configuration at its lower portion and comprising an oblong shape at its upper portion for providing superior biomedical function of the joint being supported;

said aperture having reinforcement for assisting in sealing and shaping said center aperture of said pneumatic chamber;

said pneumatic chamber further having air flow direction means for assisting the ideal shape for said pneumatic chamber;

said air flow direction means of said pneumatic chamber comprising reinforced layers forming flaring outside edges on said pneumatic chamber;

said pneumatic chamber further having valving means for permitting the inflation and deflation of said pneumatic chamber as desired by the individual using said apparatus; and shape enhancing means for maintaining the shape of said knee and elbow joint brace apparatus.

2. A knee and elbow joint brace apparatus, according to claim 1, wherein:

said valving means of said pneumatic chamber comprises a unit constructed of rubber and plastic materials;

said valving means of said pneumatic chamber further comprises an inflation bulb;

said valving means further comprises an air tube connected on one end to said inflation bulb and on the other end to said pneumatic chamber; and said inflation bulb having release means attached thereto to release the air pressure as desired.

3. A knee and elbow brace apparatus, according to claim 1, wherein:

said shape enhancing means comprises at least one spiral wire stay that is attached one each side of said apparatus for assisting in the maintenance of the shape of said apparatus.

* * * * *